US006211348B1

(12) United States Patent
Narandja et al.

(10) Patent No.: US 6,211,348 B1
(45) Date of Patent: Apr. 3, 2001

(54) HYDROXY DERIVATIVES OF TYLOSIN AND PROCESS FOR THEIR PREPARATION

(75) Inventors: Amalija Narandja; Nevenka Lopotar; Zoran Mandić, all of Zagreb (HR)

(73) Assignee: PLIVA, farmaceutska industrija, dionicko drustvo, Zagreb (HR)

( * ) Notice: Subject to any disclaimer, the term of this patent is extended or adjusted under 35 U.S.C. 154(b) by 0 days.

(21) Appl. No.: 09/393,322

(22) Filed: Sep. 10, 1999

(30) Foreign Application Priority Data

Sep. 10, 1999 (HR) ........................................ P980496A

(51) Int. Cl.[7] ........................ C07H 17/08; C07H 1/00
(52) U.S. Cl. ........................................ 536/7; 536/18.5
(58) Field of Search ................................ 536/7.1, 18.5

(56) References Cited

U.S. PATENT DOCUMENTS 5,688,924 * 11/1997 Narandja et al. .................... 536/7.1

* cited by examiner

*Primary Examiner*—Elli Peselev
(74) *Attorney, Agent, or Firm*—Connolly Bove Lodge & Hutz

(57) ABSTRACT

The present invention relates to 12,13-dihydroxy derivatives of tylosin, new semisynthetic compounds of the macrolide class, and to a process for their preparation. According to the present invention by the oxidation of 13-hydroxy derivative a 12,13-dihydroxy compound is obtained, which can be subsequently subjected to a series of reactions such as oximation, reduction (catalytic, electrochemical) or hydrolysis yielding corresponding dihydro or tetrahydro 12,13-dihydroxy derivatives.

23 Claims, No Drawings

HYDROXY DERIVATIVES OF TYLOSIN AND PROCESS FOR THEIR PREPARATION

TECHNICAL FIELD

International Patent Classification: A 61 K 31/70, C 07 H 17/08

TECHNICAL PROBLEM

The present invention relates to tylosin derivatives, new synthetic products of the macrolide class exhibiting antimicrobial activity. It particularly relates to 12,13-dihydroxy tylosin derivatives of the formula (I)

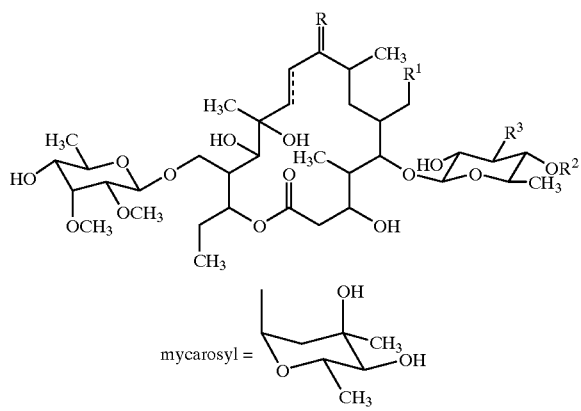

wherein
R represents O, $R_1$ represents CHO, CH=NOH or $CH(OCH_3)_2$, $R^2$ represents H or mycarosyl, $R^3$ represents $N(CH_3)_2$ or $NO(CH_3)_2$, and - - - line represents a single or a double bond, with the proviso that $R^3$ represents $N(CH_3)_2$ when - - - line represents a single bond;
wherein
R represents NOH, $R_1$ represents CHO or $CH(OCH_3)_2$, $R^2$ represents H or mycarosyl,
$R^3$ represents $N(CH_3)_2$ or $NO(CH_3)_2$, and - - - line represents a single or a double bond, with the proviso that $R^3$ represents $N(CH_3)_2$ when - - - line represents a single bond;
and to a process for their preparation.

PRIOR ART

It is known that 13-hydroxy derivatives of tylosin have been prepared by the reductive opening of the oxirane ring of 12,13-epoxy tylosin derivative, followed by catalytic hydrogenation, oximation or hydrolysis reactions (A.Narandja, SI 9700281).

According to the known prior art, the introduction of a second hydroxyl group and the formation of a vicinal diol have not been described as yet, therefore 12,13-dihydroxy derivatives of tylosin represent novel, hitherto not described compounds, which is also true of processes for their preparation.

TECHNICAL SOLUTION

It has been found that 12,13-dihydroxy tylosin derivatives of the formula

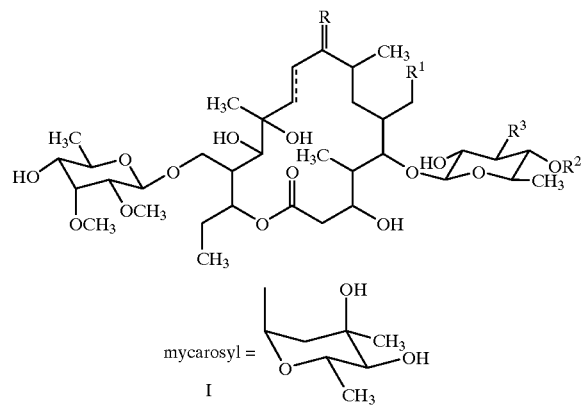

wherein
R represents O, $R_1$ represents CHO, CH=NOH or $CH(OCH_3)_2$, $R^2$ represents H or mycarosyl, $R^3$ represents $N(CH_3)_2$ or $NO(CH_3)_2$, and - - - line represents a single or a double bond, with the proviso that $R^3$ represents $N(CH_3)_2$ when - - - line represents a single bond;
wherein
R represents NOH, $R^1$ represents CHO or $CH(OCH_3)_2$, $R^2$ represents H or mycarosyl,
$R^3$ represents $N(CH_3)_2$ or $NO(CH_3)_2$, and - - - line represents a single or a double bond, with the proviso that $R^3$ represents $N(CH_3)_2$ when - - - line represents a single bond;
can be prepared by subjecting a compound of the formula (II)

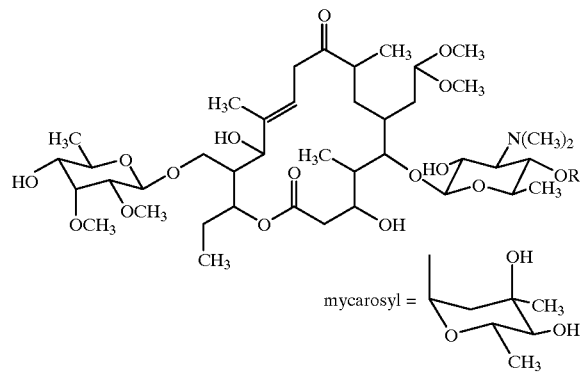

wherein R represents H or mycarosyl, dissolved in a halogenated hydrocarbon, preferably in methylene chloride, to an oxidation reaction with 3 to 8 equivalents of m-chloroperbenzoic acid within 6 to 20 hours at room temperature, whereupon, optionally,
a compound of formula I, wherein
R represents O, $R_1$ represents $CH(OCH_3)_2$, $R^2$ represents H or mycarosyl, $R^3$ represents $NO(CH_3)_2$, and - - - line represents a double bond, is subjected:
A/ to a reduction of N-oxide with Zn-powder in a mixture of lower $C_1$–$C_3$-aliphatic alcohol and water under the addition of 3–5% w/v of ammonium chloride at a pH value of 2 to 7, preferably in the range of 5.0 to 5.5 at room temperature within 3 to 6 hours, or optionally B/ to a reduction of N-oxide and $C_{10}$–$C_{11}$ double bond B1/ by a catalytic hydrogenation process in an organic solvent, preferably in a lower $C_1$–$C_3$ aliphatic alcohol in the presence of 2 to 5% w/w palladium on charcoal at a hydrogen pressure of 0.2 to 0.5 MPa at room temperature within 5 to 8 hours;

or optionally

B2/ by an electrochemical reduction process in an electrochemical cell with separate anode and cathode compartments, wherein there are used a Hg-basin as a working electrode (cathode), graphite as a counter electrode and a saturated calomel electrode as a reference electrode, in a phosphate buffer (pH=5.4) at a constant potential of −1.4 V towards the saturated calomel electrode at room temperature within 40 minutes and a charge waste of 80 C;

or optionally,

C/ to an oximation reaction with 1 to 8 equivalents of hydroxylamine hydrochloride in pyridine or a lower $C_1$–$C_3$ aliphatic alcohol under the addition of a base (pyridine or $Na_2CO_3$) in a nitrogen stream at room temperature or reflux temperature within 1 to 10 hours, or optionally, a compound of formula (I), wherein R represents NOH, $R_1$ represents $CH(OCH_3)_2$, $R^2$ represents H or mycarosyl, $R^3$ represents $NO(CH_3)_2$, and - - - line represents a double bond, is subjected to the reduction of N-oxide according to process A, or optionally, to the reduction of N-oxide and the double bond by the catalytic hydrogenation as described under B1, or optionally, a compound of the formula (I), wherein R represents O, $R_1$ represents $CH(OCH_3)_2$, $R^2$ represents H or mycarosyl, $R^3$ represents $N(CH_3)_2$, and - - - line represents a single or a double bond, is subjected to the oximation reaction as described under C, or optionally, a compound of formula (I), wherein R represents NOH, $R_1$ represents $CH(OCH_3)_2$, $R^2$ represents H or mycarosyl, $R^3$ represents $N(CH_3)_2$, and - - - line represents a single or a double bond, is subjected to hydrolysis in a mixture of acetonitrile and 0.2 N HCl (2:1) or of acetonitrile and 1% aqueous solution of trifluoroacetic acid (1:2) at room temperature within 2 hours, or optionally, a compound of formula (I), wherein R represents O, $R_1$ represents CHO, $R^2$ represents H or mycarosyl, $R^3$ represents $N(CH_3)_2$, and - - - line represents a single or a double bond, is subjected to the oximation reaction as described under C.

According to the present invention the novel compounds are isolated by conventional extraction processes from aqueous alkaline solutions by the use of halogenated hydrocarbons such as methylene chloride, chloroform or tetrachloromethane, and by evaporation to a dry residue.

The reaction course is followed by chromatography on thin layer of silica gel (Merck 60 $F_{254}$) in a solvent system: methylene chloride-methanol-ammonium hydroxide 25% (90:9:1.5, system E), (90:9:0.5, system E1) or chloroform-methanol-ammonium hydroxide 25% (95:15:1.5, system AJ). If appropriate, the separation of the reaction products and the purification of the products for the purpose of spectral analyses are performed on a silica gel column (Merck 60, 230-400 mesh/ASTM, or 60-230 mesh/ASTM in solvent system E, E1 or AJ). The identification of the novel compounds is performed by UV and NMR spectroscopies and by mass analysis.

The novel compounds show antibacterial activity, but can also be used as intermediates for the preparation of new derivatives.

The present invention is illustrated but in no way limited by the following Examples.

EXAMPLE 1

12,13-dihydro-12,13-dihydroxy-desmycosin(3'N-oxide) 20-dimethyl acetal (1)

10,13-dihydro-13-hydroxy-desmycosin 20-dimethyl acetal (10 g, 12 mmole) was dissolved in methylene chloride (150 ml), m-chloroperbenzoic acid 71% (11.6 g, 48 mmole) was added and it was stirred at room temperature for 8 hours. The reaction solution was poured into 400 ml of water, alkalized to a pH value of 8.5 by the addition of 20% NaOH, stirred for 30 minutes and, subsequently, after the removal of the organic layer, extracted once more by a mixture of methylene chloride and i-propanol (5:1). The combined extracts were washed with a saturated $NaHCO_3$ solution, dried and evaporated to a dry residue. The crude product (6.92 g) was purified by chromatography on a column (system E).

Obtained: 4.5 g (43.3%) Rf(E) 0.35, $MH^+$868; UV (EtOH) $\lambda_{max}$ 230 nm, log ε 3.88; $^1$H-NMR ($CDCl_3$) δ ppm 6.84 (1H, d, H-11), 6.41 (1H, d, H-10), 4.52 (1H, d, 1'''), 4.50 (1H, m, H-20), 4.34 (1H, d, 1), 3.60 (3H, s, 3'''OMe), 3.44 (6H, s, N-Me, 2'''OMe), 3.34 (3H, s, 20-OMe), 3.29 (3H, s, 20-OMe), 3.25 (3H, s, N-Me); $^{13}$C-NMR ($CDCl_3$) δ ppm 204.4 (s, C-9), 172.2 (s, C-1), 148.7 (d, C-11), 127.9 (d, C-10), 104.6 (d, C-1', C-20), 99.7 (d, C-1'''), 76.2 (s, C-12), 75.4 (d, C-13), 61.3 (q, 3'''OMe, N-Me), 57.4 (q, 2'''OMe), 54.0 (q, 20-OMe, NMe), 51.8 (q, 20 OMe).

EXAMPLE 2

12,13-dihydro-12,13-dihydroxy-desmycosin(3'N-oxide)-9(E+Z)oxime 20-dimethyl acetal (2)

Compound 1 (3 g, 3.45 mmole) was dissolved in dry pyridine (25 ml), hydroxylamine hydrochloride (1.92 g, 27.6 mmole) was added and it was stirred in a nitrogen stream for 5 hours at room temperature. The reaction mixture was poured into 150 ml of water, alkalized to a pH-value of 9, whereupon pyridine was removed by azeotropic distillation. An extraction with a mixture of $CHCl_3$ and i-PrOH (5:1) was performed and the combined extracts were dried and evaporated to a dry residue. The crude product (2.45 g) was subjected to chromatography on a silica gel column (system AJ).

Obtained: 0.58 g (51.7%) Rf(E1) 0.28, $MH^+$883; UV (EtOH) $\lambda_{max}$ 230 rnm, log ε 3.71; $^1$H-NMR (DMSO-$d_6$) δ ppm 10.79, 10.37 (1H, s, 9-NOH), disappear by agitation with $D_2O$; $^1$H-NMR ($CDCl_3$) δ ppm 6.25 (1H, d, H-11), 6.11 (1H, d, H-10), 4.52 (1H, d, 1'''), 4.50 (1H, m, H-20), 4.33 (1H, d, 1'), 3.61 (3H, s, 3'''OMe), 3.45 (6H, s, N-Me, 2'''OMe), 3.36 (3H, s, 20-OMe), 3.32 (3H, s, 20-OMe), 3.26 (3H, s, N-Me); $^{13}$C-NMR ($CDCl_3$) δ ppm 171.8, 170.9 (s, C-1), 163.8, 159.0 (s, C-9), 143.2, 142.2 (d, C-11), 123.3, 115.3 (d, C-10), 104.7 (d, C-1', C-20), 99.6 (d, C-1'''), 76.6 (s, C-12), 75.7 (d, C-13), 61.3 (q, 3'''OMe, N-Me), 57.4 (q, 2'''OMe), 54.0 (q, 20-OMe, NMe), 51.8 (q, 20-OMe).

EXAMPLE 3

12,13-dihydro-12,13-dihydroxy-tylosin (3'N-oxide) 20-dimethyl acetal (3)

10,13-dihydro-13-hydroxy-tylosin 20-dimethyl acetal (2.0 g, 2 mmole) was dissolved in methylene chloride (30 ml), m-chloroperbenzoic acid 71% (2.18 g, 9 mmole) was added and it was stirred at room temperature for 8 hours, whereupon the isolation as described in Example 1 was performed.

Obtained: 0.67 g (33%/) Rf(E1) 0.55, MH$^+$1012; UV (EtOH) $\lambda_{max}$ 230 nm, log $\epsilon$ 3.58; $^1$H-NMR (CDCl$_3$) $\delta$ ppm 6.82 (1H, d, H-11), 6.39 (1H, d, H-10), 5.08 (1H, d, 1''), 4.55 (1H, d, 1'''), 4.50 (1H, m, H-20), 4.34 (1H, d, 1'), 3.60 (3H, s, 3'''OMe), 3.44 (6H, s, NMe, 2'''OMe), 3.34 (3H, s, 20-OMe), 3.29 (3H, s, 20-OMe), 3.25 (3H, s, N-Me); $^{13}$C-NMR (CDCl$_3$) $\delta$ ppm 203.6 (s, C-9), 172.2 (s, C-1) 148.7 (d, C-11), 127.9 (d, C-10), 104.6 (d, C-1', C-20), 99.7 (d, C-1'''), 97.1 (d, C-1''), 61.3 (q, 3'''OMe, N-Me), 57.4 (q, 2'''OMe), 54.0 (q, 20-OMe, NMe), 51.8 (q, 20-OMe).

EXAMPLE 4

12,13-dihydro-12,13-dihydroxy-desmycosin 20-dimethyl acetal (4)

Compound 1 (1 g, 1.15 mmole) was dissolved in 35% ethanol (60 ml), 3.1 g of NH$_4$Cl and stepwise 1 g of Zn under maintaining the pH-value of 5.0–5.5 were added. It was stirred at room temperature for 5 hours, whereupon Zn was separated by filtration and EtOH was removed by evaporation at reduced pressure. The aqueous solution was alkalized to a pH-value of 8.5, whereupon extraction with chloroform was performed. The extracts were dried and evaporated to a dry residue.

Obtained: 0.83 g (84.6%) Rf(E) 0.48, Rf (E1) 0.43, MH$^+$852; UV (EtOH) $\lambda_{max}$ 230 nm, log $\epsilon$ 3.91; $^1$H-NMR (CDCl$_3$) $\delta$ ppm 6.83 (1H, d, H-11), 6.39 (1H, d, H-10), 4.51 (1H, d, 1'''), 4.49 (1H, m, H-20), 4.35 (1H, d, 1'), 3.60 (3H, s, 3'''OMe), 3.44 (3H, s, 2'''OMe), 3.34 (3H, s, 20-OMe), 3.29 (3H, s, 20-OMe), 2.50 (6H, s, NMe$_2$)$_3$; $^{13}$C-NMR (CDCl$_3$) $\delta$ ppm 204.5 (s, C-9), 172.3 (s, C-1) 148.9 (d, C-11), 127.9 (d, C-10), 104.6 (d, C-1', C-20), 99.8 (d, C-1'''), 76.4 (s, C-12), 75.4 (d, C-13), 61.3 (q, 3'''OMe), 57.4 (q, 2'''OMe, 54.0 (q, 20-OMe), 51.8 (q, 20-OMe), 40.1 (q, NMe$_2$).

EXAMPLE 5

12,13-dihydroxy-10,11,12,13-tetrahydroy-desmycosin 20-dimethyl acetal (5)

Process A

Compound 1 (1 g, 1.15 mmole) was dissolved in ethanol (50 ml), 0.5 g of 10% Pd/C were added and it was hydrogenated for 8 hours at a hydrogen pressure of 0.5 MPa at room temperature, whereupon the catalyst was separated by filtration and ethanol was evaporated to a dry residue.

Obtained: 0.88 g (90%/o) Rf(E) 0.45, MH$^+$854; does not absorb in UV; $^1$H-NMR (CDCl$_3$) $\delta$ ppm 4.55 (1H, d, 1'''), 4.52 (1H, m, H-20), 4.35 (1H, d, 1'), 3.60 (3H, s, 3'''OMe), 3.44 (3H, s, 2'''OMe), 3.34 (3H, s, 20-OMe), 3.29 (3H, s, 20-OMe), 2.50 (6H, s, NMe$_2$); $^{13}$C-NMR (CDCl$_3$) $\delta$ ppm 212.4 (s, C-9), 173.0 (s, C-1) 104.6 (d, C-1', C-20), 99.7 (d, C1'''), 61.3 (q, 3'''OMe), 57.4 (q, 2'''OMe), 54.0 (q, 20-OMe), 51.8 (q, 20-OMe), 40.1 (q, NMe$_2$).

Process B

Compound 1 (0.2 g, 0.23 mmole) was dissolved in 50 ml of phosphate buffer (pH=5.4) and then it was transferred into an electrochemical cell having separate anode and cathode compartments. The Hg-basin was used as a working electrode (cathode), whereas graphite was used as a counter electrode and a saturated calomel electrode was used as a reference electrode. The reaction was performed under a constant potential of −1.4 V towards the saturated calomel electrode at room temperature within 40 minutes at a charge waste of 80 C. The reaction solution was alkalized to a pH-value of 8.5 and extracted with chloroform. The extract was washed with a saturated NaHCO$_3$ solution and evaporated to a dry residue.

Obtained: 0.16 g (81.6%) Rf(E) 0.45, Rf(E1) 0.43, MH$^+$854 and the spectral characteristics as in the compound obtained by process 5A.

EXAMPLE 6

12,13-dihydroxy-10,11,12,13-tetrahydro-desmycosin-9(E+Z) oxime 20-dimethyl acetal (6)

Compound 2 (1 g, 1.13 mmole) was dissolved in ethanol (50 ml), 0.5 g of 10% Pd/C were added and it was hydrogenated for 9 hours at a hydrogen pressure of 0.5 MPa at room temperature, whereupon the catalyst was separated by filtration and ethanol was evaporated to a dry residue.

Obtained: 0.85 g (88%) Rf(E1) 0.43, MH$^+$869; does not absorb in UV; $^1$H-NMR (DMSO-d$_6$) $\delta$ ppm 10.69, 10.49 (1H, s, 9-NOH), dissapear by agitation with D$_2$O; $^1$H-NMR (CDCl$_3$) $\delta$ ppm 4.51 (1H, d, 1'''), 4.50 (1H, m, H-20), 4.32 (1H, d, 1'), 3.61 (3H, s, 3'''OMe), 3.45 (3H, s, 2'''OMe), 3.36 (3H, s, 20-OMe), 3.32 (3H, s, 20-OMe), 2.51 (6H, s, NMe$_2$); $^{13}$C-NMR (CDCl$_3$) $\delta$ ppm 172.5 (s, C-1), 165.6, 162.3 (s, C-9), 104.7 (d, C-1'), 104.5 (d, C-20), 99.6 (d, C-1'''), 61.3 (q, 3'''OMe), 57.4 (q, 2'''OMe), 54.0 (q, 20-OMe), 51.8 (q, 20-OMe).

EXAMPLE 7

12,13-dihydro-12,13-dihydroxy-desmycosin-9(E+Z) oxime 20-dimethyl acetal (7)

Compound 4 (2 g, 2.34 mmole) was dissolved in dry pyridine (25 ml), hydroxylamine hydrochloride (1.9 g, 27.6 mmole) was added and it was stirred in a nitrogen stream for 6 hours at room temperature. The isolation was performed as described in Example 2.

Obtained: 1.14 g (55.9%) Rf(E1) 0.39, MH$^+$867; UV (EtOH) $\lambda_{max}$ 231 nm, log $\epsilon$ 3.97; $^1$H-NMR (DMSO-d$_6$) $\delta$ ppm 10.77, 10.49 (1H, s, 9-NOH), dissapear by agitation with D$_2$O; $^1$H-NMR (CDCl$_3$) $\delta$ ppm 6.23 (1H, d, H-11), 6.09 (1H, d, H-10), 4.52 (1H, d, 1'''), 4.50 (1H, m, H-20), 4.33 (1H, d, 1'), 3.61 (3H, s, 3'''OMe), 3.45 (3H, s, 2'''OMe), 3.36 (3H, s, 20-OMe), 3.32 (3H, s, 20-OMe), 2.50 (6H, s, NMe$_2$); $^{13}$C-NMR (CDCl$_3$) $\delta$ ppm 171.9 (s, C-1), 163.6, 159.2 (s, C-9), 148.7, 143.8 (d, C-11), 123.6, 116.0 (d, C-10), 104.7 (d, C-1', C-20), 99.6 (d, C-1'''), 76.6 (s, C-12), 75.5 (d, C-13), 61.3 (q, 3'''-OMe), 57.4 (q, 2'''OMe), 54.0 (q, 20-OMe), 51.8 (q, 20-OMe), 40.3 (q, NMe$_2$).

EXAMPLE 8

12,13-dihydro-12,13-dihydroxy-desmycosin-9(E+Z) oxime (8)

Compound 7 (0.5 g, 0.58 mmole) was dissolved in acetonitrile (5 ml) and in 1% aqueous trifluoroacetic acid solution (10 ml) and it was stirred at room temperature for 2 hours. To the reaction mixture chloroform (8 ml) was added and it was alkalized to a pH-value of 8.5. One more extraction with chloroform was performed. The combined extracts were washed with 1% NaHCO$_3$ solution, dried and evaporated to a dry residue.

Obtained: 0.4 g (85%) Rf (E1) 0.30, MH$^+$821; UV (EtOH) $\lambda_{max}$ 232 nm, log ε 3.47; $^1$H-NMR (DMSO-d$_6$) δ ppm 10.75, 10.48 (1H, s, 9-NOH), dissapear by agitation with D$_2$O; $^1$H-NMR (CDCl$_3$) δ ppm 9.67 (1H, s, H-20), 6.24 (1H, d, H-11), 6.10 (1H, d, H-10), 4.52 (1H, d, 1'''), 4.33 (1H, d, 1'), 3.61 (3H, s, 3'''OMe), 3.45 (3H, s, 2'''OMe), 2.50 (6H, s, NMe$_2$); $^{13}$(C-NMR (CDCl$_3$) δ ppm 203.1 (d, C-20), 172.9 (s, C-1), 163.2, 159.6 (s, C-9), 148.7 (d, C-11), 123.8, 115.9 (d, C-10), 104.7 (d, C-1'), 99.6 (d, C-1'''), 61.3 (q, 3'''OMe), 57.4 (q, 2'''OMe), 40.3 (q, NMe$_2$).

EXAMPLE 9

12,13-dihydro-12,13-dihydroxy-desmycosin (9)

Compound 4 (1 g, 1.17 mmole) was dissolved in acetonitrile (10 ml) and in 1% aqueous trifluoroacetic acid solution (18 ml) and then hydrolysis and isolation were performed as in Example 8.

Obtained: 0.75 g (80%) Rf(E) 0.42, MH$^+$806; UV (EtOH) $\lambda_{max}$ 230 nm, log ε 3.79; $^1$H-NMR (CDCl$_3$) δ ppm 9.68 (1H, s, H-20), 6.81 (1H, d, H-11), 6.39 (1H, d, H-10), 4.52 (1H, d, 1'''), 4.33 (1H, d, 1'), 3.61 (3H, s, 3'''OMe), 3.45 (3H, s, 2'''OMe), 2.50 (6H, s, NMe$_2$); $^{13}$C-NMR (CDCl$_3$) δ ppm 203.2 (s, C-9), 203.1 (d, C-20), 172.9 (s, C-1), 148.7 (d, C-11), 124.0 (d, C-10), 104.7 (d, C-1'), 99.6 (d, C1'''), 61.3 (q, 3'''OMe), 57.4 (q, 2'''OMe), 40.3 (q, NMe$_2$).

EXAMPLE 10

12,13-dihydro-12,13-dihydroxy-desmycosin-20-oxime (10)

Compound 9 (0.5 g, 0.62 mmole) was dissolved in ethanol (10 ml), pyridine (0.3 ml) and hydroxylamine hydrochloride (0.043 g, 0.62 mmole) were added and it was stirred in a nitrogen stream for 1 hour at room temperature. To the reaction mixture water (10 ml) was added and it was alkalized to a pH-value of 9 and evaporated to ⅓ of its volume. An extraction with chloroform at pH 5.5 (5 ml) and pH 9.0 (2×5 ml) was performed. The combined extracts (pH 9) were evaporated to a dry residue.

Obtained: 0.28 g (55%) Rf(E1) 0.35, MH$^+$821; UV (EtOH) $\lambda_{max}$ 230 nm, log ε 3.67; $^1$H-NMR (DMSO-d$_6$) δ ppm 10.37 (1H, s, 20-NOH), dissapears by agitation with D$_2$O, $^1$H-NMR (CDCl$_3$) δ ppm 6.81 (1H, d, H-11), 6.39 (1H, d, H-10), 4.52 (1H, d, 1'''), 4.33 (1H, d, 1'), 3.61 (3H, s, 3'''OMe), 3.45 (3H, s, 2'''OMe), 2.50 (6H, s, NMe$_2$); $^{13}$C-NMR (CDCl$_3$) δ ppm 203.2 (s, C-9), 172.9 (s, C-1), 151.5 (d, C-20), 148.8 (d, C-11), 123.8 (d, C-10), 104.7 (d, C-1'), 99.6 (d, C1'''), 61.3 (q, 3'''OMe), 57.4 (q, 2'''OMe), 40.3 (q, NMe$_2$).

What is claimed is:
1. 12,13-dihydroxy derivative of tylosin of the formula (I)

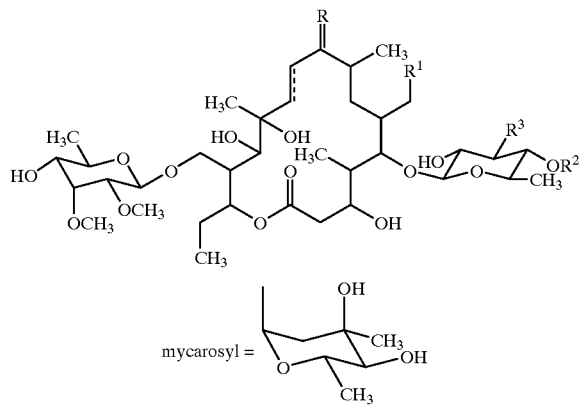

wherein
R represents O, R$^1$ represents CHO, CH=NOH or CH(OCH$_3$)$_2$, R$^2$ represents H or mycarosyl, R$^3$ represents N(CH$_3$)$_2$ or NO(CH$_3$)$_2$, and - - - line represents a single or a double bond, with the proviso that R$^3$ represents N(CH$_3$)$_2$ when - - - line represents a single bond; or
wherein
R represents NOH, R$^1$ represents CHO or CH(OCH$_3$)$_2$, R$^2$ represents H or mycarosyl, R$^3$ represents N(CH$_3$)$_2$ or NO(CH$_3$)$_2$, and - - - line represents a single or a double bond, with the proviso that R$^3$ represents N(CH$_3$)$_2$ when - - - line represents a single bond.

2. A tylosin derivative according to claim 1, wherein R represents O, R$^1$ represents CH(OCH$_3$)$_2$, R$^2$ represents H, R$^3$ represents NO(CH$_3$)$_2$, and - - - line represents a double bond.

3. The tylosin derivative according to claim 1, wherein R represents O, R$^1$ represents CH(OCH$_3$)$_2$, R$^2$ represents mycarosyl, R$^3$ represents NO(CH$_3$)$_2$, and - - - line represents a double bond.

4. The tylosin derivative according to claim 1, wherein R represents NOH, R$^1$ represents CH(OCH$_3$)$_2$, R$^2$ represents H, R$^3$ represents NO(CH$_3$)$_2$, and - - - line represents a double bond.

5. The tylosin derivative according to claim 1, wherein R represents O, R$^1$ represents CH(OCH$_3$)$_2$, R$^2$ represents H, R$^3$ represents N(CH$_3$)$_2$, and - - - line represents a double bond.

6. The tylosin derivative according to claim 1, wherein R represents O, R$^1$ represents CH(OCH$_3$)$_2$, R$^2$ represents H, R$^3$ represents N(CH$_3$)$_2$, and - - - line represents a single bond.

7. The tylosin derivative according to claim 1, wherein R represents NOH, R$^1$ represents CH(OCH$_3$)$_2$, R$^2$ represents H, R$^3$ represents N(CH$_3$)$_2$, and - - - line represents a single bond.

8. The tylosin derivative according to claim 1, wherein R represents NOH, R$^1$ represents CH(OCH$_3$)$_2$, R$^2$ represents H, R$^3$ represents N(CH$_3$)$_2$, and - - - line represents a double bond.

9. The tylosin derivative according to claim 1, wherein R represents NOH, R$^1$ represents CHO, R$^2$ represents H, R$^3$ represents N(CH$_3$)$_2$, and - - - line represents a double bond.

10. The tylosin derivative according to claim 1, wherein R represents O, R$^1$ represents CHO, R$^2$ represents H, R$^3$ represents N(CH$_3$)$_2$, and - - - line represents a double bond.

11. The tylosin derivative according to claim 1, wherein R represents O, $R^1$ represents CH=NOH, $R^2$ represents H, $R^3$ represents $N(CH_3)_2$, and - - - line represents a double bond.

12. A process for the preparation of a 12,13-dihydroxy tylosin derivative of the formula (I):

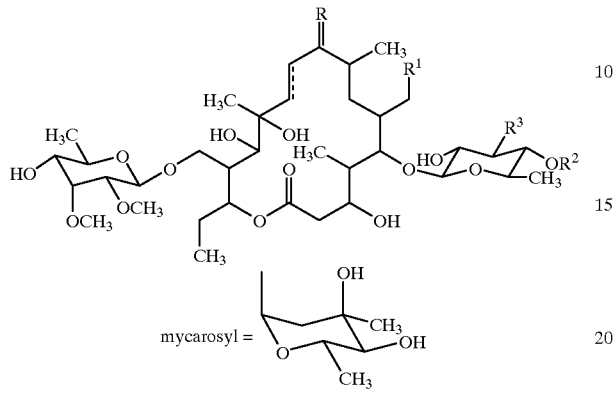

wherein
R represents O, $R^1$ represents CHO, CH=NOH or $CH(OCH_3)_2$, $R^2$ represents H or mycarosyl, $R^3$ represents $N(CH_3)_2$ or $NO(CH_3)_2$ and - - - line represents a single or a double bond, with the proviso that $R^3$ represents $N(CH_3)_2$ when - - - line represents a single bond; or wherein
R represents NOH, $R_1$ represents CHO or $CH(OCH_3)_2$, $R^2$ represents H or mycarosyl, $R^3$ represents $N(CH_3)_2$ or $NO(CH_3)_2$ and - - - line represents a single or a double bond, with the proviso that $R^3$ represents $N(CH_3)_2$ when - - - line represents a single bond, wherein a compound of the formula (II):

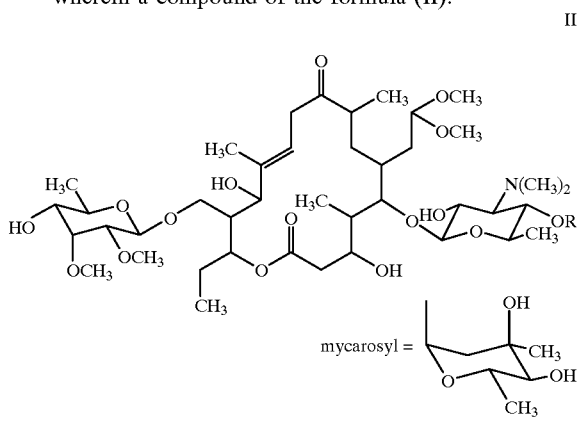

wherein R represents H or mycarosyl, is subjected to an oxidation reaction, yielding a tylosin derivative having the formula I, wherein R represents O, $R^1$ represents $CH(OCH_3)_2$, $R^2$ represents H or mycarosyl, $R^3$ represents $NO(CH_3)_2$, and - - - line represents a double bond, said tylosin derivative is optionally subjected:

A/ to a reduction of N-oxide; or optionally

B/ to a reduction of N-oxide and $C_{10}$–$C_{11}$ double bond; or optionally

C/ to an oximation reaction; or optionally a compound of formula (I), wherein R represents NOH, $R^1$ represents $CH(OCH_3)_2$, $R^2$ represents H or mycarosyl, $R^3$ represents $NO(CH_3)_2$, and - - - line represents a double bond, is subjected to a reduction of N-oxide; or optionally to a reduction of N-oxide and $C_{10}$–$C_{11}$ double bond by catalytic hydrogenation;

or optionally a compound of the formula (I), wherein R represents O, $R_1$ represents $CH(OCH_3)_2$, $R^2$ represents H or mycarosyl, $R^3$ represents $N(CH_3)_2$, and - - - line represents a single or a double bond, is subjected to an oximation reaction; or optionally a compound of formula (I), wherein R represents NOH, $R^1$ represents $CH(OCH_3)_2$, $R^2$ represents H or mycarosyl, $R^3$ represents $N(CH_3)_2$, and - - - line represents a single or a double bond, subjected to hydrolysis.

13. A process according to claim 12, wherein said oxidation is performed with 3 to 8 equivalents of m-chloroperbenzoic acid in a halogenated hydrocarbon.

14. A process according to claim 13, wherein said reduction of N-oxide is performed with Zn-powder in a mixture of a lower $C_1$–$C_3$ aliphatic alcohol and water (1:2) under the addition of 3 to 5% w/v of ammonium chloride at a pH-value of 2 to 7.

15. A process according to claim 12, wherein said reduction of N-oxide and $C_{10}$–$C_{11}$ double bond is performed by catalytic hydrogenation in an organic solvent in the presence of 2 to 5% w/v of palladium on charcoal at a hydrogen pressure of 0.2 to 0.5 MPa at room temperature for from about 5 to about 8 hours.

16. A process according to claim 12, wherein said reduction of N-oxide and $C_{10}$–$C_{11}$ double bond is performed by electrochemical reduction in an electrochemical cell having separate anode and cathode compartments, wherein a Hg-basin is used as a working electrode (cathode), graphite is used as a counter electrode and a saturated calomel electrode is used as a reference electrode and wherein the pH is maintained at about 5.4 by a phosphate buffer at a constant potential of −1.4 V towards the saturated calomel electrode at room temperature within 40 minutes and a charge waste of 80 C.

17. A process according to claim 12, wherein said oximation is performed with about 1 to 8 equivalents of hydroxylamine hydrochloride in a pyridine or lower $C_1$–$C_3$ aliphatic alcohol under the addition of a base in a nitrogen stream at room temperature or at reflux temperature for about 1 to 10 hours.

18. A process according to claim 12, wherein said hydrolysis is performed in a mixture of acetonitrile and 0.2 N HCl (2:1) or of acetonitrile and 1% aqueous solution of trifluoroacetic acid (1:2) at room temperature for about 2 hours.

19. The process according to claim 13, wherein said halogenated hydrocarbon is methylene chloride and wherein said process is performed for from about 6 to about 20 hours at approximately room temperature.

20. The process according to claim 14, wherein said pH is from about 5.0 to about 5.5 and wherein said process is performed for from about 3 to about 6 hours at approximately room temperature.

21. The process according to claim 15, wherein said organic solvent is lower $C_1$–$C_3$-aliphatic alcohol.

22. The process according to claim 17, wherein said base is selected from the group consisting of pyridine and $Na_2CO_3$.

23. The process according to claim 18, wherein said hydrolysis is performed in a 1:2 mixture of acetonitrile and 1% aqueous solution of trifluoroacetic acid.

* * * * *